United States Patent
Hinger

(10) Patent No.: US 10,503,309 B2
(45) Date of Patent: Dec. 10, 2019

(54) DRIVE SCHEME FOR ULTRASONIC TRANSDUCER PIXEL READOUT

(71) Applicant: QUALCOMM Incorporated, San Diego, CA (US)

(72) Inventor: Ashish Hinger, Sunnyvale, CA (US)

(73) Assignee: QUALCOMM Incorporated, San Diego, CA (US)

(*) Notice: Subject to any disclaimer, the term of this patent is extended or adjusted under 35 U.S.C. 154(b) by 119 days.

(21) Appl. No.: 15/474,084

(22) Filed: Mar. 30, 2017

(65) Prior Publication Data
US 2017/0285877 A1    Oct. 5, 2017

Related U.S. Application Data

(60) Provisional application No. 62/318,117, filed on Apr. 4, 2016.

(51) Int. Cl.
| | |
|---|---|
| *G06F 3/043* | (2006.01) |
| *G06F 3/041* | (2006.01) |
| *G06K 9/00* | (2006.01) |

(52) U.S. Cl.
CPC ......... *G06F 3/0416* (2013.01); *G06K 9/0002* (2013.01)

(58) Field of Classification Search
CPC ... G06F 3/0436; G06F 3/0416; A61B 5/1172; B06B 1/0622; G01N 29/26
See application file for complete search history.

(56) References Cited

U.S. PATENT DOCUMENTS

| | | | | |
|---|---|---|---|---|
| 4,977,601 A | * | 12/1990 | Bicz | A61B 5/1172 356/71 |
| 2005/0163353 A1 | * | 7/2005 | Schneider | G06K 9/0002 382/124 |
| 2011/0050039 A1 | * | 3/2011 | Toda | B06B 1/0622 310/327 |
| 2011/0215150 A1 | * | 9/2011 | Schneider | G06K 9/0002 235/439 |

(Continued)

FOREIGN PATENT DOCUMENTS

| | | |
|---|---|---|
| JP | S62231187 A | 10/1987 |
| WO | WO-9849691 A2 | 11/1998 |

(Continued)

OTHER PUBLICATIONS

International Search Report and Written Opinion—PCT/US2017/025358—ISA/EPO—dated Jul. 11, 2017.

*Primary Examiner* — Benyam Ketema
(74) *Attorney, Agent, or Firm* — Weaver Austin Villeneuve & Sampson LLP; Robert A. Reid

(57) ABSTRACT

This disclosure provides some implementations of systems, methods and apparatus associated with a drive scheme for ultrasonic transducer pixel readout. In some implementations, a piezoelectric ultrasonic transducer has a first electrode, a second electrode, and a piezoelectric layer disposed between the first and second electrodes. The second electrode is coupled with a sampling node. A sampling diode has an input and an output. The input is coupled to receive a diode bias signal. The output is coupled with the sampling node. Controller circuitry is configured to control the diode bias signal to at least partially drive a voltage at the sampling node. Read circuitry is coupled with the sampling node to read the voltage.

15 Claims, 9 Drawing Sheets

(56) References Cited

U.S. PATENT DOCUMENTS

| | | | | |
|---|---|---|---|---|
| 2014/0354596 | A1* | 12/2014 | Djordjev | G06K 9/0002 |
| | | | | 345/175 |
| 2014/0354597 | A1* | 12/2014 | Kitchens, II | G06F 1/3215 |
| | | | | 345/175 |
| 2014/0354905 | A1* | 12/2014 | Kitchens | G06F 1/3215 |
| | | | | 349/12 |
| 2015/0015515 | A1 | 1/2015 | Dickinson et al. | |
| 2015/0016223 | A1* | 1/2015 | Dickinson | G06F 3/043 |
| | | | | 367/87 |
| 2015/0241393 | A1* | 8/2015 | Ganti | G01N 29/09 |
| | | | | 73/589 |
| 2017/0285877 | A1* | 10/2017 | Hinger | G06F 3/0436 |
| 2018/0101711 | A1* | 4/2018 | D'Souza | G06F 21/32 |

FOREIGN PATENT DOCUMENTS

| | | |
|---|---|---|
| WO | WO-2015066330 A1 | 5/2015 |
| WO | WO-2015127335 A2 | 8/2015 |

\* cited by examiner

DRIVE SCHEME FOR ULTRASONIC TRANSDUCER PIXEL READOUT

PRIORITY DATA

This patent document claims priority under 35 U.S.C. § 119(e) to commonly assigned U.S. Provisional Patent Application No. 62/318,117, by Hinger, titled DRIVE SCHEME FOR ULTRASONIC TRANSDUCER PIXEL READOUT, filed Apr. 4, 2016, which is hereby incorporated by reference.

TECHNICAL FIELD

This disclosure relates to piezoelectric ultrasonic transducers and, in some implementations, to an electronic sensor array or interactive display of piezoelectric transducers for biometric sensing, imaging, and touch or gesture recognition.

DESCRIPTION OF THE RELATED TECHNOLOGY

Ultrasonic sensor systems may use a transmitter to generate and send an ultrasonic wave through a transmissive medium and towards an object to be detected. The ultrasonic transmitter may be operatively coupled to an ultrasonic sensor array configured to detect portions of the ultrasonic wave that are reflected from the object. For example, in ultrasonic fingerprint sensors, an ultrasonic pulse may be produced by starting and stopping the transmitter during a short interval of time. At each material interface encountered by the ultrasonic pulse, a portion of the ultrasonic pulse may be reflected.

Piezoelectric ultrasonic transducers are attractive candidates for numerous applications such as biometric sensor systems including fingerprint sensors, gesture detection systems, microphones and speakers, ultrasonic imaging systems and chemical sensors. Such transducers can incorporate a piezoelectric material as a receiver for detecting ultrasonic signals. A piezoelectric ultrasonic transducer typically includes a piezoelectric stack suspended over a cavity. The piezoelectric stack may include a layer of piezoelectric material and a layer of patterned or unpatterned electrodes on each side of the piezoelectric layer.

SUMMARY

The systems, methods and devices of this disclosure each have several innovative aspects, no single one of which is solely responsible for the desirable attributes disclosed herein.

In some aspects, an apparatus includes a piezoelectric ultrasonic transducer having a first electrode, a second electrode, and a piezoelectric layer disposed between the first and second electrodes. The second electrode is coupled with a sampling node. A sampling diode has an input and an output. The input is coupled to receive a diode bias signal. The output is coupled with the sampling node. Controller circuitry is configured to control the diode bias signal to at least partially drive a voltage at the sampling node. Read circuitry is coupled with the sampling node to read the voltage.

In some implementations, the controller circuitry is configured to control the diode bias signal to switch between two voltage levels including a first level and a second level. The second level is asserted during a sampling window corresponding to activation of the read circuitry. For example, the first level can correspond to a normal mode of operation of the read circuitry, and the second level can correspond to a sampling mode of operation of the read circuitry.

In some implementations, a substrate is disposed adjacent to the second electrode opposite the piezoelectric layer. The substrate can be a thin-film transistor (TFT) layer and can include the sampling diode. In some instances, a reset transistor is formed in the TFT layer and coupled with the sampling diode to control resetting of the voltage.

In some implementations, the first electrode is coupled with a ground terminal, a DC voltage source, or a fixed AC voltage source. In some other implementations, the first electrode is floating.

In some implementations, the apparatus further includes a touch controller coupled with the first electrode, and the touch controller is configured to provide touch control of the piezoelectric layer. In some implementations, the apparatus further includes a platen disposed adjacent to the first electrode opposite the piezoelectric layer.

In some aspects, a method includes providing a diode bias signal to a sampling diode coupled with a sampling node. Transmission of an ultrasonic signal is initiated using a piezoelectric ultrasonic transducer as described above. The piezoelectric ultrasonic transducer is capable of receiving a reflected portion of the ultrasonic signal and generating a response characteristic based on the reflected portion of the ultrasonic signal. The diode bias signal can be controlled to bias the diode in association with a temporary transition of a mode of operation from a normal mode to a sampling mode. During the sampling mode of operation, sampling of an electrical signal at the sampling node is enabled. In some implementations, the method further includes resetting a voltage at the sampling node using a reset switch coupled with the diode.

In some aspects, a non-transitory computer readable medium stores program code to be executed by one or more processors. The program code includes instructions configured to cause: providing a diode bias signal to a sampling diode coupled with a sampling node; initiating transmission of an ultrasonic signal using a piezoelectric ultrasonic transducer as described above; controlling the diode bias signal to bias the diode in association with a temporary transition of a mode of operation from a normal mode to a sampling mode; and enabling sampling, during the sampling mode of operation, of an electrical signal at the sampling node.

BRIEF DESCRIPTION OF THE DRAWINGS

Details of one or more implementations of the subject matter described in this specification are set forth in the accompanying drawings and the description below. Other features, aspects and advantages will become apparent from the description, the drawings and the claims. Note that the relative dimensions of the drawings and other diagrams of this disclosure may not be drawn to scale. The sizes, thicknesses, arrangements, materials, etc., shown and described in this disclosure are made only by way of example and should not be construed as limiting. Like reference numbers and designations in the various drawings indicate like elements.

DETAILED DESCRIPTION

Figure 1:
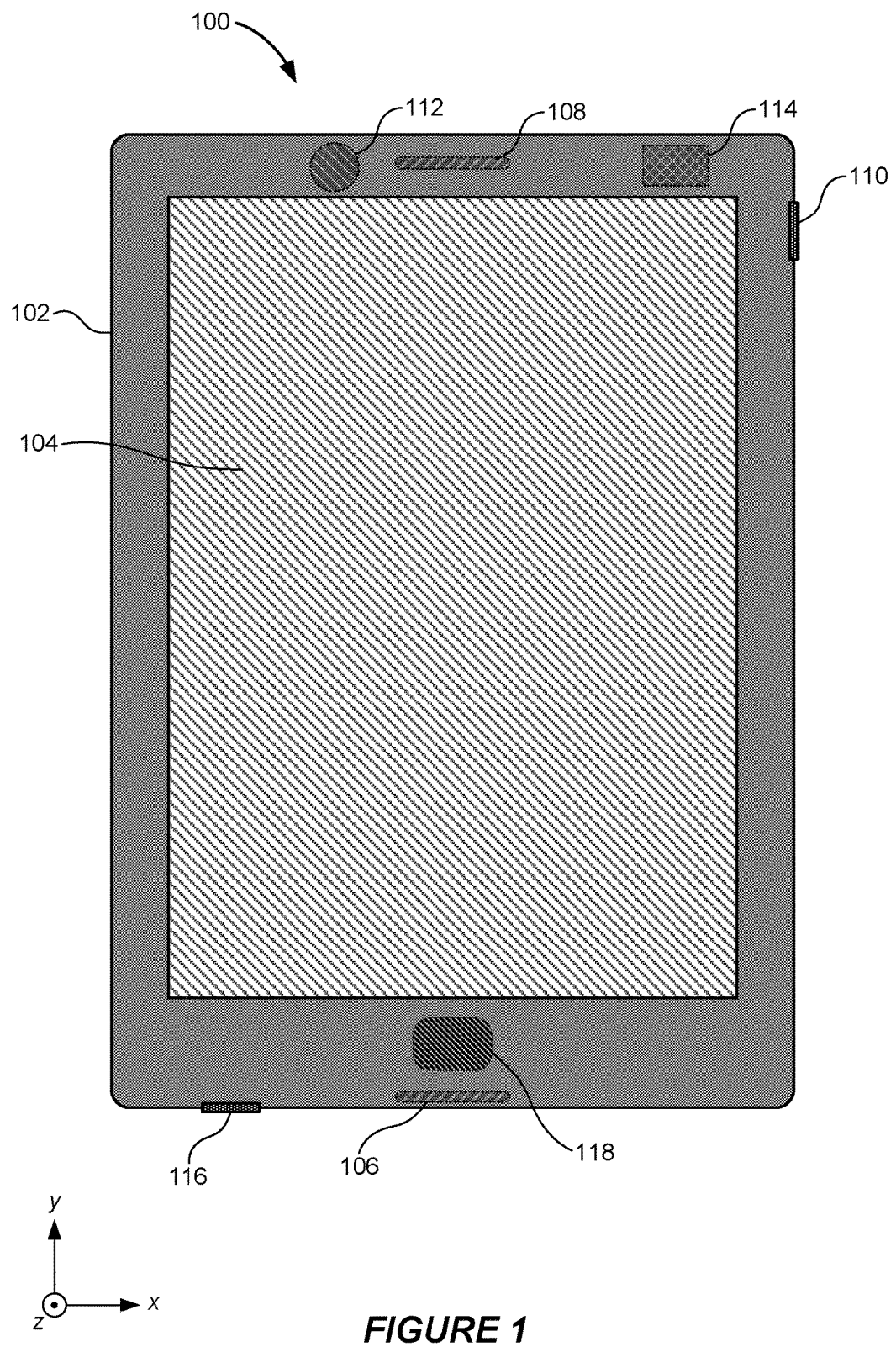
FIG. 1 shows a front view of a diagrammatic representation of an example of a mobile device 100 that includes an ultrasonic sensing system according to some implementations.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system for ultrasonic sensing. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headband, patches, etc., Bluetooth® devices, personal data assistants (PDAs), wireless electronic mail receivers, hand-held or portable computers, netbooks, notebooks, smartbooks, tablet computers, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, steering wheels or other automobile parts, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

By way of example, some fingerprint sensors may be implemented with an ultrasonic sensor system using piezoelectric material for the transmission and receiving of ultrasonic waves. For example, a voltage applied across piezoelectric material corresponding to a transmitter may result in the piezoelectric material stretching or contracting, e.g., being deformed such that the material is strained in response to the applied voltage, resulting in the generation of the ultrasonic wave, as previously discussed. The reflected signals (e.g., the reflected portions of the ultrasonic wave, as previously discussed) may result in the stretching or contracting of piezoelectric material corresponding to a receiver. This results in the generation of a surface charge, and therefore, a voltage across the piezoelectric material that may be used as an electrical output signal representing a portion of raw image data that represents fingerprint image data.

Some implementations of the subject matter described in this disclosure provide an efficient drive scheme for pixel readout with biasing of the pixel of an ultrasonic sensor incorporating a thin film piezoelectric material. In some implementations, the ultrasonic sensor includes a top electrode or layer of electrodes and a bottom electrode or layer of electrodes sandwiching a layer of the piezoelectric material. A platen is often mounted on the top electrode (opposite the piezoelectric layer). The bottom electrode is coupled to a sampling diode. When a bias signal, DBias, is applied to the diode, one or more pixels formed from the bottom electrode can be effectively driven by controlling the DBias waveform. For instance, DBias can have two voltage levels. For readout of a pixel, sampling can be optimized by incorporating the diode in conjunction with the DBias signal. In some implementations, the top electrode can be grounded, kept at a contact DC voltage or even left floating without affecting image quality and overall system performance.

Particular implementations of the subject matter described in this disclosure may be implemented to realize one or more of the following potential advantages. By driving the diode coupled to the pixel, in some implementations, it is not necessary to connect the top electrode to an amplifier and to an associated RBias sampling signal, a constraint of some conventional systems. In such conventional systems, an amplifier such as a class AB amp can consume large amounts of power and require high frequencies (e.g., 128 MHz) for operation, as well as be costly and occupy significant space in a design. In some of the disclosed implementations, voltage swings of DBias can be lower than a conventional three-level high-voltage-swing RBias signal to reduce power consumption in the system. Also, reducing the number of components in the system (by eliminating an amplifier) can provide cost savings and reduce chip real estate. Some implementations are less sensitive to resistance on an electrical path through the top electrode, where the resistance can be affected by various laminating material and the platen. Also, in some implementations, image quality is not affected in the case of unwanted platen shortening during manufacturing or usage. This can result in better electrostatic discharge (ESD) protection for the overall system especially via the top electrode. In addition, based on the capacitance load of the diode, the pixel can be sampled at higher sampling frequencies.

FIG. 1 shows a front view of a diagrammatic representation of an example of a mobile device 100 that includes an ultrasonic sensing system according to some implementations. The mobile device 100 may be representative of, for example, various portable computing devices such as cellular phones, smartphones, multimedia devices, personal gaming devices, tablet computers and laptop computers, among other types of portable computing devices. However, various implementations described herein are not limited in application to portable computing devices. Indeed, various techniques and principles disclosed herein may be applied in traditionally non-portable devices and systems, such as in computer monitors, television displays, kiosks, vehicle navigation devices and audio systems, among other applications. Additionally, various implementations described herein are not limited in application to devices that include displays.

The mobile device 100 generally includes a housing (or "case") 102 within which various circuits, sensors and other electrical components reside. In the illustrated example implementation, the mobile device 100 also includes a touchscreen display (also referred to herein as a "touch-sensitive display") 104. The touchscreen display 104 generally includes a display and a touchscreen arranged over or otherwise incorporated into or integrated with the display. The display 104 may generally be representative of any of a variety of suitable display types that employ any of a variety of suitable display technologies. For example, the display 104 may be a digital micro-shutter (DMS)-based display, a light-emitting diode (LED) display, an organic LED (OLED) display, a liquid crystal display (LCD), an LCD display that uses LEDs as backlights, a plasma display, an interferometric modulator (IMOD)-based display, or another type of display suitable for use in conjunction with touch-sensitive user interface (UI) systems.

The mobile device 100 may include various other devices or components for interacting with, or otherwise communicating information to or receiving information from, a user. For example, the mobile device 100 may include one or more microphones 106, one or more speakers 108, and in some cases one or more at least partially mechanical buttons 110. The mobile device 100 may include various other components enabling additional features such as, for example, one or more video or still-image cameras 112, one or more wireless network interfaces 114 (for example, Bluetooth, WiFi or cellular) and one or more non-wireless interfaces 116 (for example, a universal serial bus (USB) interface or an HDMI interface).

The mobile device 100 may include an ultrasonic sensing system 118 capable of scanning and imaging an object signature, such as a fingerprint, palm print or handprint. In some implementations, the ultrasonic sensing system 118 may function as a touch-sensitive control button. In some implementations, a touch-sensitive control button may be implemented with a mechanical or electrical pressure-sensitive system that is positioned under or otherwise integrated with the ultrasonic sensing system 118. In other words, in some implementations, a region occupied by the ultrasonic sensing system 118 may function both as a user input button to control the mobile device 100 as well as a fingerprint sensor to enable security features such as user authentication features.

Figure 2A:
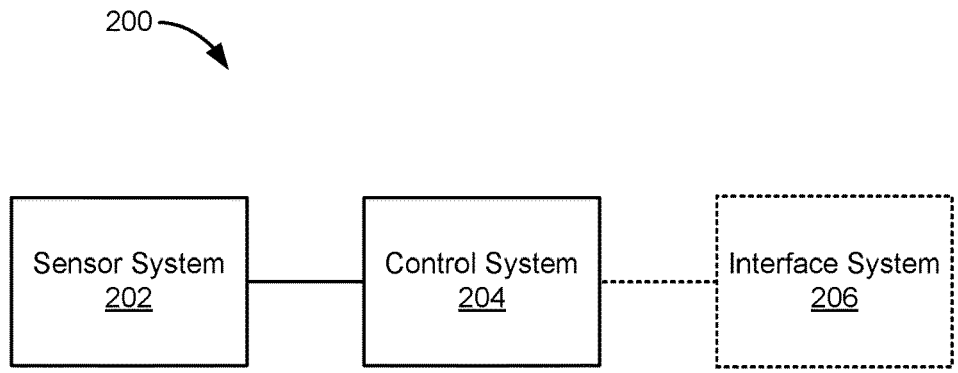
FIG. 2A shows a block diagram representation of components of an example of an ultrasonic sensing system 200 according to some implementations.

FIG. 2A shows a block diagram representation of components of an example of an ultrasonic sensing system 200 according to some implementations. As shown, the ultrasonic sensing system 200 may include a sensor system 202 and a control system 204 electrically coupled to the sensor system 202. The sensor system 202 may be capable of scanning an object and providing raw measured image data usable to obtain an object signature, for example, such as a fingerprint of a human finger. The control system 204 may be capable of controlling the sensor system 202 and processing the raw measured image data received from the sensor system. In some implementations, the ultrasonic sensing system 200 may include an interface system 206 capable of transmitting or receiving data, such as raw or processed measured image data, to or from various components within or integrated with the ultrasonic sensing system 200 or, in some implementations, to or from various components, devices or other systems external to the ultrasonic sensing system.

Figure 2B:
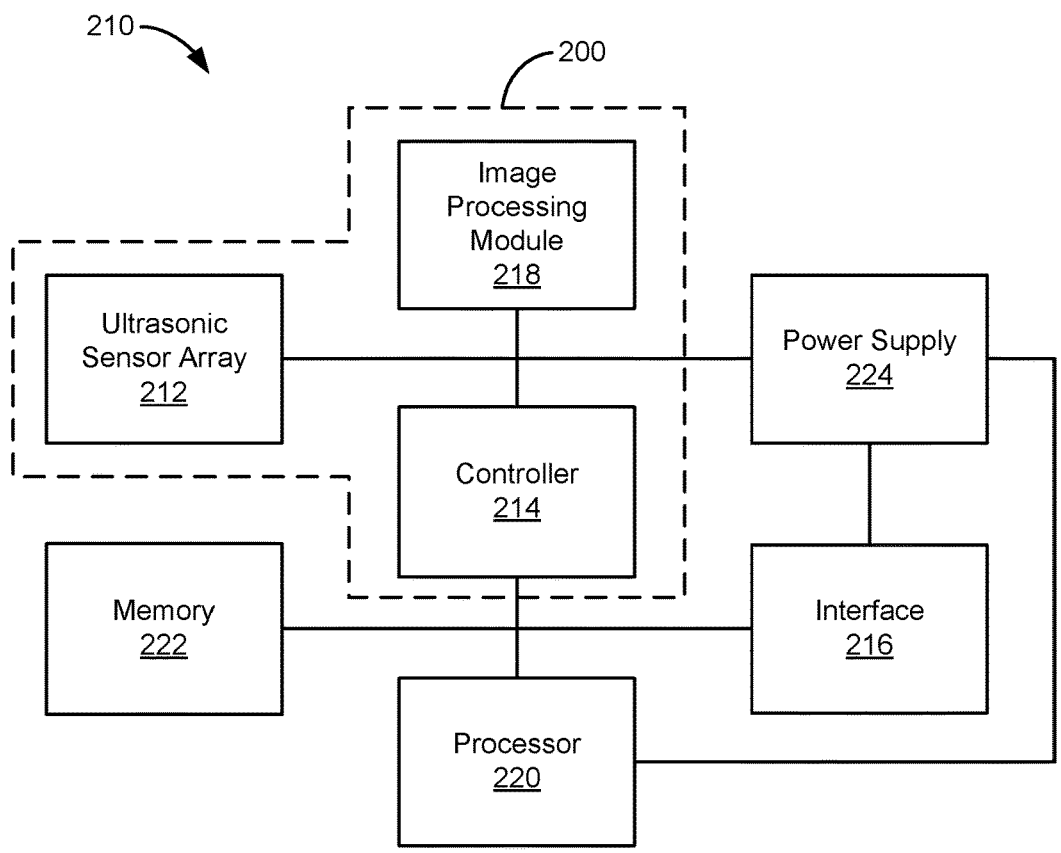
FIG. 2B shows a block diagram representation of components of an example of a mobile device 210 that includes the ultrasonic sensing system of FIG. 2A.

FIG. 2B shows a block diagram representation of components of an example of a mobile device 210 that includes the ultrasonic sensing system 200 of FIG. 2A. For example, the mobile device 210 may be a block diagram representation of the mobile device 100 shown in and described with reference to FIG. 1 above. The sensor system 202 of the ultrasonic sensing system 200 of the mobile device 210 may be implemented with an ultrasonic sensor array 212. The control system 204 of the ultrasonic sensing system 200 may be implemented with a controller 214 that is electrically coupled to the ultrasonic sensor array 212. While the controller 214 is shown and described as a single component, in some implementations, the controller 214 may collectively refer to two or more distinct control units or processing units in electrical communication with one another. In some implementations, the controller 214 may include one or more of a general purpose single- or multi-chip processor, a central processing unit (CPU), a digital signal processor (DSP), an applications processor, an application specific integrated circuit (ASIC), a field programmable gate array (FPGA) or other programmable logic device (PLD), discrete gate or transistor logic, discrete hardware components, or any combination thereof designed to perform the functions and operations described herein.

The ultrasonic sensing system 200 of FIG. 2B may include an image processing module 218. In some implementations, raw measured image data provided by the ultrasonic sensor array 212 may be sent, transmitted, communicated or otherwise provided to the image processing module 218. The image processing module 218 may include any suitable combination of hardware, firmware and software configured, adapted or otherwise operable to process the image data provided by the ultrasonic sensor array 212. In some implementations, the image processing module 218 may include signal or image processing circuits or circuit components including, for example, amplifiers (such as instrumentation amplifiers or buffer amplifiers), analog or digital mixers or multipliers, switches, analog-to-digital converters (ADCs), passive or active analog filters, among others. In some implementations, one or more of such circuits or circuit components may be integrated within the controller 214, for example, where the controller 214 is implemented as a system-on-chip (SoC) or system-in-package (SIP). In some implementations, one or more of such circuits or circuit components may be integrated within a DSP included within or coupled to the controller 214. In some implementations, the image processing module 218 may be implemented at least partially via software. For example, one or more functions of, or operations performed by, one or more of the circuits or circuit components just described may instead be performed by one or more software modules executing, for example, in a processing unit of the controller 214 (such as in a general purpose processor or a DSP).

In some implementations, in addition to the ultrasonic sensing system 200, the mobile device 210 may include a separate processor 220, a memory 222, an interface 216 and a power supply 224. In some implementations, the controller 214 of the ultrasonic sensing system 200 may control the ultrasonic sensor array 212 and the image processing module 218, and the processor 220 of the mobile device 210 may control other components of the mobile device 210. In some implementations, the processor 220 communicates data to the controller 214 including, for example, instructions or commands. In some such implementations, the controller 214 may communicate data to the processor 220 including, for example, raw or processed image data. It should also be understood that, in some other implementations, the functionality of the controller 214 may be implemented entirely, or at least partially, by the processor 220. In some such implementations, a separate controller 214 for the ultrasonic sensing system 200 may not be required because the functions of the controller 214 may be performed by the processor 220 of the mobile device 210.

Depending on the implementation, one or both of the controller 214 and processor 220 may store data in the memory 222. For example, the data stored in the memory 222 may include raw measured image data, filtered or otherwise processed image data, estimated PSF or estimated image data, and final refined PSF or final refined image data. The memory 222 may store processor-executable code or other executable computer-readable instructions capable of execution by one or both of the controller 214 and the processor 220 to perform various operations (or to cause other components such as the ultrasonic sensor array 212, the image processing module 218, or other modules to perform operations), including any of the calculations, computations, estimations or other determinations described herein (including those presented in any of the equations below). It should also be understood that the memory 222 may collectively refer to one or more memory devices (or "components"). For example, depending on the implementation, the controller 214 may have access to and store data in a different memory device than the processor 220. In some implementations, one or more of the memory components may be implemented as a NOR- or NAND-based Flash memory array. In some other implementations, one or more of the memory components may be implemented as a different type of non-volatile memory. Additionally, in some implementations, one or more of the memory components may include a volatile memory array such as, for example, a type of RAM.

In some implementations, the controller 214 or the processor 220 may communicate data stored in the memory 222 or data received directly from the image processing module 218 through an interface 216. For example, such communicated data can include image data or data derived or otherwise determined from image data. The interface 216 may collectively refer to one or more interfaces of one or more various types. In some implementations, the interface 216 may include a memory interface for receiving data from or storing data to an external memory such as a removable memory device. Additionally or alternatively, the interface 216 may include one or more wireless network interfaces or one or more wired network interfaces enabling the transfer of raw or processed data to, as well as the reception of data from, an external computing device, system or server.

A power supply 224 may provide power to some or all of the components in the mobile device 210. The power supply 224 may include one or more of a variety of energy storage devices. For example, the power supply 224 may include a rechargeable battery, such as a nickel-cadmium battery or a lithium-ion battery. Additionally or alternatively, the power supply 224 may include one or more supercapacitors. In some implementations, the power supply 224 may be chargeable (or "rechargeable") using power accessed from, for example, a wall socket (or "outlet") or a photovoltaic device (or "solar cell" or "solar cell array") integrated with the mobile device 210. Additionally or alternatively, the power supply 224 may be wirelessly chargeable.

As used hereinafter, the term "processing unit" refers to any combination of one or more of a controller of an ultrasonic system (for example, the controller 214), an image processing module (for example, the image processing module 218), or a separate processor of a device that includes the ultrasonic system (for example, the processor 220). In other words, operations that are described below as being performed by or using a processing unit may be performed by one or more of a controller of the ultrasonic system, an image processing module, or a separate processor of a device that includes the ultrasonic sensing system.

Figure 3A:
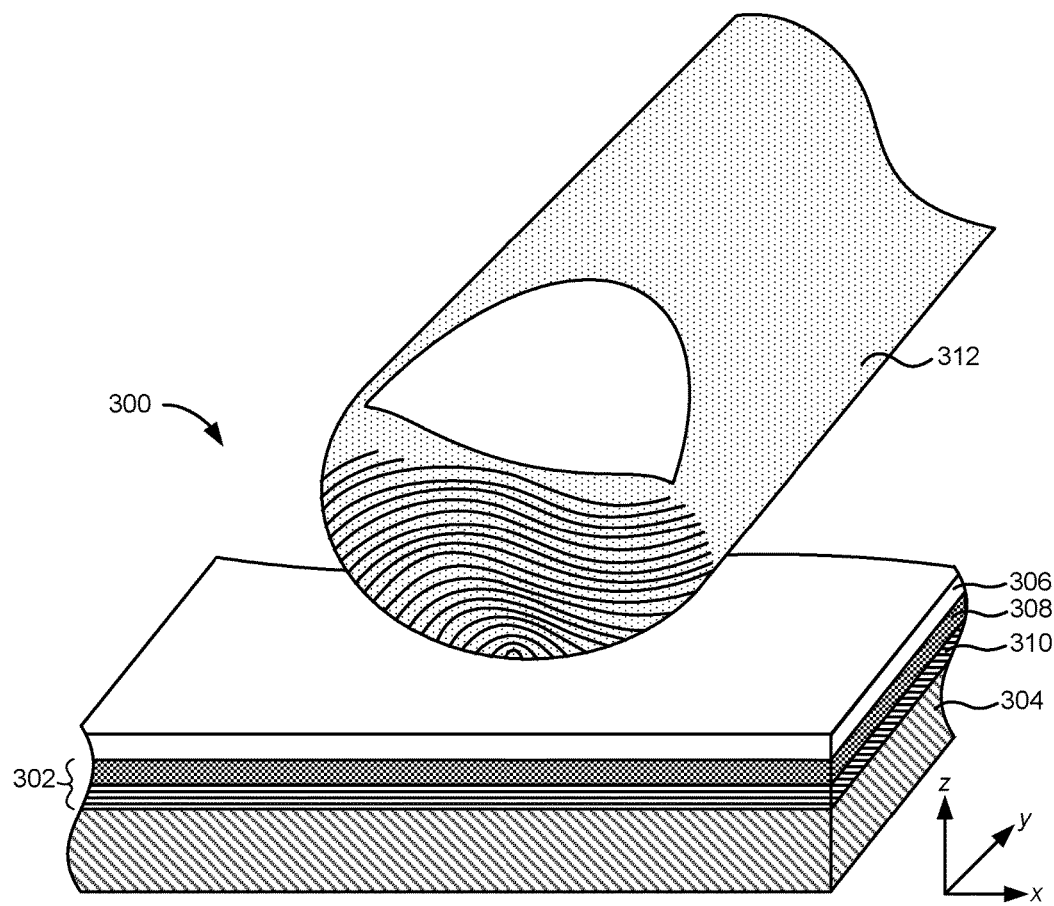
FIG. 3A shows a cross-sectional projection view of a diagrammatic representation of a portion of an example of an ultrasonic sensing system 300 according to some implementations.
Figure 3B:
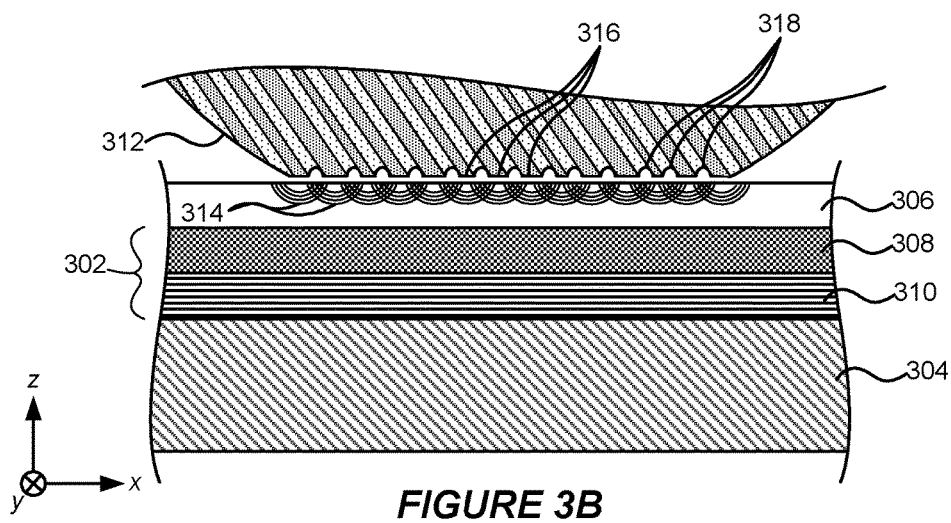
FIG. 3B shows a zoomed-in cross-sectional side view of the ultrasonic sensing system of FIG. 3A according to some implementations.

FIG. 3A shows a cross-sectional projection view of a diagrammatic representation of a portion of an example of an ultrasonic sensing system 300 according to some implementations. FIG. 3B shows a zoomed-in cross-sectional side view of the ultrasonic sensing system of FIG. 3A according to some implementations. For example, the ultrasonic sensing system 300 may implement the ultrasonic sensing system 118 described with reference to FIG. 1 or the ultrasonic sensing system 200 shown and described with reference to FIGS. 2A and 2B. The ultrasonic sensing system 300 may include an ultrasonic transducer 302 that overlies a substrate 304 and that underlies a platen (a "cover plate" or "cover glass") 306. The ultrasonic transducer 302 may include both an ultrasonic transmitter 308 and an ultrasonic receiver 310.

The ultrasonic transmitter 308 is generally configured to generate ultrasonic waves towards the platen 306, and in the illustrated implementation, towards a human finger positioned on the upper surface of the platen. In some implementations, the ultrasonic transmitter 308 may more specifically be configured to generate ultrasonic plane waves towards the platen 306. In some implementations, the ultrasonic transmitter 308 includes a layer of piezoelectric material such as, for example, polyvinylidene fluoride (PVDF) or a PVDF copolymer such as PVDF-TrFE. For example, the piezoelectric material of the ultrasonic transmitter 308 may be configured to convert electrical signals provided by the controller of the ultrasonic sensing system into a continuous or pulsed sequence of ultrasonic plane waves at a scanning frequency. In some implementations, the ultrasonic transmitter 308 may additionally or alternatively include capacitive ultrasonic devices.

Figure 4:
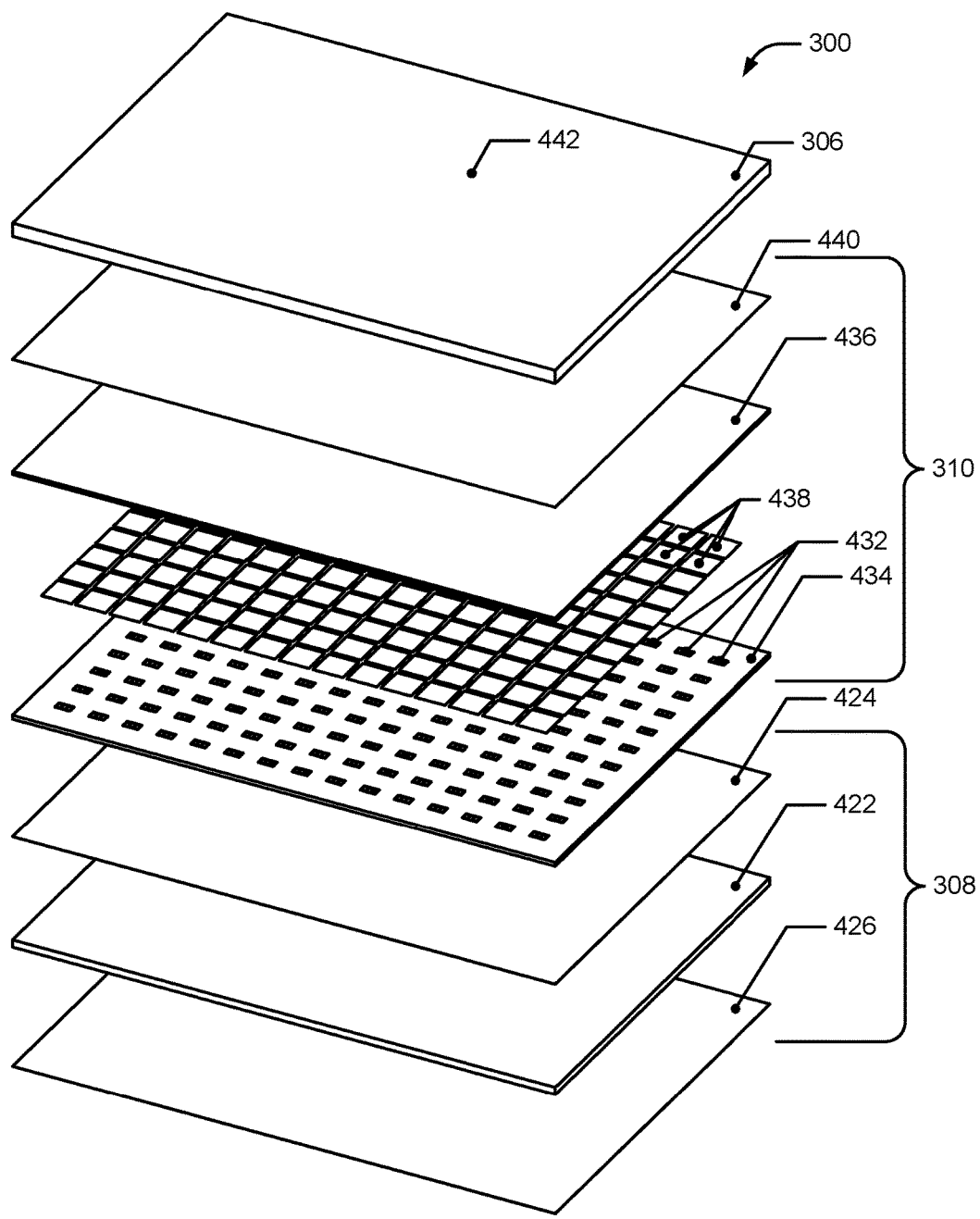
FIG. 4 shows an exploded projection view of an example of components of the ultrasonic sensing system of FIGS. 3A and 3B according to some implementations.

The ultrasonic receiver 310 is generally configured to detect ultrasonic reflections 314 resulting from interactions of the ultrasonic waves transmitted by the ultrasonic transmitter 308 with ridges 316 and valleys 318 defining the fingerprint of the finger 312 being scanned. In some implementations, the ultrasonic transmitter 308 overlies the ultrasonic receiver 310 as, for example, illustrated in FIGS. 3A and 3B. In some other implementations, the ultrasonic receiver 310 may overlie the ultrasonic transmitter 308 (as shown in FIG. 4 described below). The ultrasonic receiver 310 may be configured to generate and output electrical output signals corresponding to the detected ultrasonic reflections. In some implementations, the ultrasonic receiver 310 may include a second piezoelectric layer different than the piezoelectric layer of the ultrasonic transmitter 308. For example, the piezoelectric material of the ultrasonic receiver 310 may be any suitable piezoelectric material such as, for example, a layer of PVDF or a PVDF copolymer. The piezoelectric layer of the ultrasonic receiver 310 may convert vibrations caused by the ultrasonic reflections into electrical output signals. In some implementations, the ultrasonic receiver 310 further includes a thin-film transistor (TFT) layer. In some such implementations, the TFT layer may include an array of sensor pixel circuits configured to amplify the electrical output signals generated by the piezoelectric layer of the ultrasonic receiver 310. The amplified electrical signals provided by the array of sensor pixel circuits may then be provided as raw measured image data to the processing unit for use in processing the image data, identifying a fingerprint associated with the image data, and in some applications, authenticating a user associated with the fingerprint. In some implementations, a single piezoelectric layer may serve as the ultrasonic transmitter 308 and the ultrasonic receiver 310. In some implementations, the substrate 304 may be a glass, plastic or silicon substrate upon which electronic circuitry may be fabricated. In some implementations, an array of sensor pixel circuits and associated interface circuitry of the ultrasonic receiver 310 may be configured from CMOS circuitry formed in or on the substrate 304. In some implementations, the substrate 304 may be positioned between the platen 306 and the ultrasonic transmitter 308 and/or the ultrasonic receiver 310. In some implementations, the substrate 304 may serve as the platen 306. One or more protective layers, acoustic matching layers, anti-smudge layers, adhesive layers, decorative layers, conductive layers or other coating layers (not shown) may be included on one or more sides of the substrate 304 and the platen 306.

The platen 306 may be formed of any suitable material that may be acoustically coupled to the ultrasonic transmitter 308. For example, the platen 306 may be formed of one or more of glass, plastic, ceramic, sapphire, metal or metal alloy. In some implementations, the platen 306 may be a cover plate such as, for example, a cover glass or a lens glass of an underlying display. In some implementations, the platen 306 may include one or more polymers, such as one or more types of parylene, and may be substantially thinner. In some implementations, the platen 306 may have a thickness in the range of about 10 microns (µm) to about 1000 µm or more.

In some implementations, the ultrasonic sensing system 300 may further include a focusing layer (not shown). For example, the focusing layer may be positioned above the ultrasonic transmitter 308. The focusing layer may generally include one or more acoustic lenses capable of altering the paths of ultrasonic waves transmitted by the ultrasonic transmitter 308. In some implementations, the lenses may be implemented as cylindrical lenses, spherical lenses or zone lenses. In some implementations, some or all of the lenses may be concave lenses, whereas in some other implementations some or all of the lenses may be convex lenses, or include a combination of concave and convex lenses.

In some implementations that include such a focusing layer, the ultrasonic sensing device 300 may additionally include an acoustic matching layer to ensure proper acoustic coupling between the focusing lens(es) and an object, such as a finger, positioned on the platen 306. For example, the acoustic matching layer may include an epoxy doped with particles that change the density of the acoustic matching layer. If the density of the acoustic matching layer is changed, then the acoustic impedance will also change according to the change in density, if the acoustic velocity remains constant. In alternative implementations, the acoustic matching layer may include silicone rubber doped with metal or with ceramic powder. In some implementations, sampling strategies for processing output signals may be implemented that take advantage of ultrasonic reflections being received through a lens of the focusing layer. For example, an ultrasonic wave coming back from a lens' focal point will travel into the lens and may propagate towards multiple receiver elements in a receiver array fulfilling the acoustic reciprocity principle. Depending on the signal strength coming back from the scattered field, an adjustment of the number of active receiver elements is possible. In general, the more receiver elements that are activated to receive the returned ultrasonic waves, the higher the signal-to-noise ratio (SNR). In some implementations, one or more acoustic matching layers may be positioned on one or both sides of the platen 306, with or without a focusing layer.

FIG. 4 shows an exploded projection view of an example of components of the example ultrasonic sensing system of FIGS. 3A and 3B according to some implementations. The ultrasonic transmitter 308 may include a substantially planar piezoelectric transmitter layer 422 capable of functioning as a plane wave generator. Ultrasonic waves may be generated by applying a voltage across the piezoelectric transmitter layer 422 to expand or contract the layer, depending upon the voltage signal applied, thereby generating a plane wave. In this example, the processing unit (not shown) is capable of causing a transmitter excitation voltage to be applied across the piezoelectric transmitter layer 422 via a first transmitter electrode 424 and a second transmitter electrode 426. The first and second transmitter electrodes 424 and 426 may be metallized electrodes, for example, metal layers that coat opposing sides of the piezoelectric transmitter layer 422. As a result of the piezoelectric effect, the applied transmitter excitation voltage causes changes in the thickness of the piezoelectric transmitter layer 422, and in such a fashion, generates ultrasonic waves at the frequency of the transmitter excitation voltage.

The ultrasonic waves may travel towards a target object, such as a finger, passing through the platen 306. A portion of the ultrasonic waves not absorbed or transmitted by the target object may be reflected back through the platen 306 and received by the ultrasonic receiver 310, which, in the implementation illustrated in FIG. 4, overlies the ultrasonic transmitter 308. The ultrasonic receiver 310 may include an array of sensor pixel circuits 432 disposed on a substrate 434 and a piezoelectric receiver layer 436. In some implementations, each sensor pixel circuit 432 may include one or more TFT or CMOS transistor elements, electrical interconnect traces and, in some implementations, one or more additional circuit elements such as diodes, capacitors, and the like. Each sensor pixel circuit 432 may be configured to convert an electric charge generated in the piezoelectric receiver layer 436 proximate to the pixel circuit into an electrical signal. Each sensor pixel circuit 432 may include a pixel input electrode 438 that electrically couples the piezoelectric receiver layer 436 to the sensor pixel circuit 432.

In the illustrated implementation, a receiver bias electrode 440 is disposed on a side of the piezoelectric receiver layer 436 proximal to the platen 306. The receiver bias electrode 440 may be a metallized electrode and may be grounded or biased to control which signals may be passed to the array of sensor pixel circuits 432. Ultrasonic energy that is reflected from the exposed (upper/top) surface 442 of the platen 306 may be converted into localized electrical charges by the piezoelectric receiver layer 436. These localized charges may be collected by the pixel input electrodes 438 and passed on to the underlying sensor pixel circuits 432. The charges may be amplified or buffered by the sensor pixel circuits 432 and provided to the processing unit. The processing unit may be electrically connected (directly or indirectly) with the first transmitter electrode 424 and the second transmitter electrode 426, as well as with the receiver bias electrode 440 and the sensor pixel circuits 432 on the substrate 434. In some implementations, the processing unit may operate substantially as described above. For example, the processing unit may be capable of processing the signals received from the sensor pixel circuits 432.

Some examples of suitable piezoelectric materials that can be used to form the piezoelectric transmitter layer 422 or the piezoelectric receiver layer 436 include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 PVDF-TrFE, 80:20 PVDF-TrFE, and 90:10 PVDR-TrFE. Other examples of piezoelectric materials that may be utilized include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 422 and the piezoelectric receiver layer 436 is selected so as to be suitable for generating and receiving ultrasonic waves, respectively. In one example, a PVDF piezoelectric transmitter layer 422 is approximately 28 μm thick and a PVDF-TrFE receiver layer 436 is approximately 12 μm thick. Example frequencies of the ultrasonic waves may be in the range of about 1 Megahertz (MHz) to about 100 MHz, with wavelengths on the order of a millimeter or less.

Figure 5:
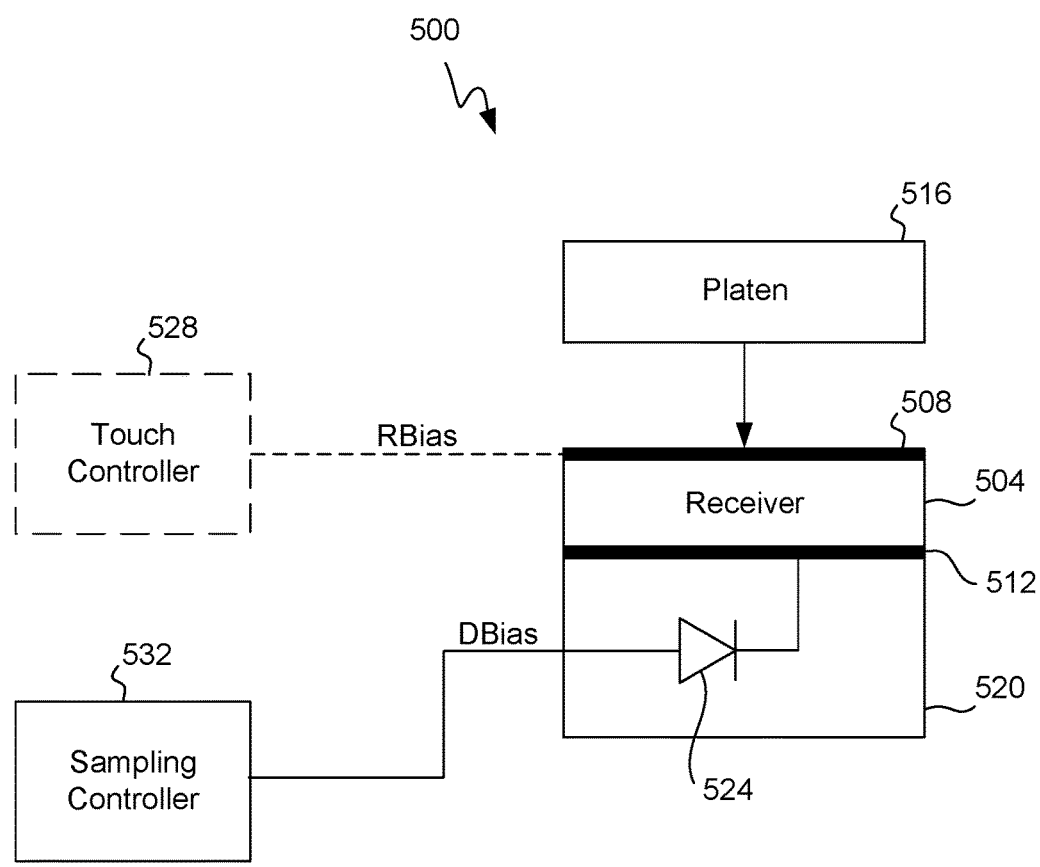
FIG. 5 shows a cross-sectional projection view of an example of an ultrasonic sensor 500 incorporating a thin film piezoelectric material to serve as a receiver according to some implementations.

FIG. 5 shows a cross-sectional projection view of an example of an ultrasonic sensor 500 incorporating a layer of thin film piezoelectric material to serve as a receiver 504 according to some implementations. The layer of piezoelectric material can be configured as a transmitter in some other implementations. The piezoelectric material can be in the form of a copolymer, a PVDF, a lead zirconate titanate (PZT) or some combination thereof, by way of example only. In some implementations, the piezoelectric layer is a single layer, while in some other implementations, the piezoelectric layer includes two or more layers.

In FIG. 5, the sensor 500 incorporates a piezoelectric transducer including the receiver 504, a top electrode 508 formed on a top side of the receiver 504 and a bottom electrode 512 formed opposite the top electrode 508 on a bottom side of the receiver 504. Those skilled in the art should appreciate that "top" and "bottom" are used herein only for purposes of convenience and description of the electrodes relative to each other; when such apparatus is in use, these electrodes can have any relative position and orientation along X, Y and Z axes as the apparatus is moved, rotated, etc. Also, the bottom electrode is sometimes referred to herein as a sampling electrode. A platen 516 is affixed to or otherwise seated above the top electrode 508 (opposite the receiver 504), for instance, with a lamination applied between the platen 516 and the top electrode 508. In the example of FIG. 5, there is no padding, contact or other conductive element or conductive layer situated between the top electrode 508 and the platen 516, so the platen 516 can sit uniformly on the top electrode 508. Also, in the example of FIG. 5, there is no amplifier such as a class AB amp electrically connected with the top electrode 508. The bottom electrode 512 is seated on a substrate 520 composed of an appropriate material such as silicon. For example, the substrate 520 can be a TFT layer of an appropriate thickness such as 500 micrometers.

In some implementations, the top electrode 508 is not electrically connected with any pixels, while one or more pixels are formed from the bottom electrode 512. In some implementations, the bottom electrode 512 is composed of Indium Tin Oxide (ITO). In some implementations, the top electrode 508 is grounded. In some other implementations, the top electrode 508 is floating. In some other implementations, a voltage source is electrically connected with the top electrode 508 to supply the top electrode 508 with a constant DC voltage. In some other implementations, an AC power supply is coupled with the top electrode 508 to provide the top electrode 508 with a fixed AC waveform.

In FIG. 5, a diode 524 is constructed in the substrate 520 with an output terminal at the diode 524's cathode electrically connected to the bottom electrode 512. In this way, the diode 524 is coupled to the receiver 504 through the bottom electrode 512. A diode bias signal, DBias, is supplied at an input terminal connected to the anode of the diode 524. DBias is a drive signal having a waveform configured to drive the receiver 504 to provide desired sampling, as explained in greater detail below. In some implementations, DBias is applied to the diode 524 to facilitate sampling in a per-pixel manner.

In some implementations, an optional touch controller 528 is in the form of an external chip or other external circuitry electrically connected with the top electrode 508. Optionally, the touch controller 528 can generate and output an RBias signal to provide touch control of the receiver 504, when desired. In such implementations, the touch controller 528 can be directly connected to the top electrode 508 without any additional coupling of an amplifier to the top electrode 508. In the example of FIG. 5, regardless of whether the touch controller 528 is connected and/or RBias is provided, and regardless of the waveform of RBias, the receiver 504 is driven with DBias, which is injected at the anode of the diode 524. In some implementations, a controller 532 with circuitry providing sampling control can generate and output DBias to the anode of the diode 524. As explained in greater detail below, the DBias signal can be asserted during a sampling period when biasing of read transistors in read circuitry (described in more detail below) is initiated to read out data. Sampling of such data can be correlated with the movement of the receiver 504 due to the coupling of the diode 524 to the receiver 504 through the bottom electrode 512.

In FIG. 5, an ultrasonic signal or pressure wave in an ultrasonic frequency band can be generated by the transducer to propagate through the platen and towards and/or into an object such as a person's finger disposed upon or above the platen (opposite the top electrode 508). When reaching the object, a portion of the pressure wave can be reflected back, causing the receiver 504 to vibrate in response to the reflected pressure wave and generate a corresponding electrical signal, as described above.

Figure 6:
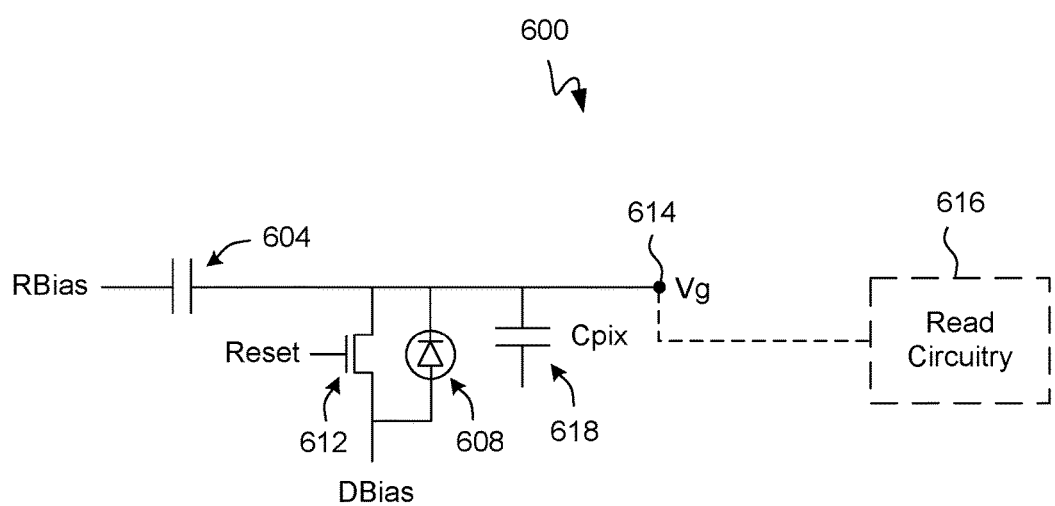
FIG. 6 shows a circuit diagram of an example of a circuit 600 modeling an ultrasonic sensor and read circuitry according to some implementations.

FIG. 6 shows a circuit diagram of an example of a circuit 600 modeling an ultrasonic sensor and read circuitry according to some implementations. In FIG. 6, an ultrasonic transducer as described above is represented as a capacitor 604, with a first (top) electrode coupled to receive RBias, as described above. A second (bottom) electrode of the capacitor 604 is coupled to the cathode of a sampling diode 608, while the anode of the diode 608 is coupled to receive DBias, as described above. A reset switch in the form of a transistor 612 is coupled in parallel with the diode 608 and driven by a Reset signal to control a resetting operation, for instance, following readout. For instance, the transistor 612 can be an NMOS TFT formed in the substrate 520 of FIG. 5. The transistor 612 can be configured to reset an output voltage, Vg, of the circuit 600 at an output node 614, also referred to as a sampling node, after Vg is captured (or read) by external read circuitry 616. As shown, the second electrode of the capacitor 604 and the cathode of the diode 608 are coupled to the output node 614. The Reset signal can be generated and controlled by a suitable controller. In FIG. 6, a capacitor 618 in the circuit 600 represents the parasitic capacitance, Cpix, of a receiver such as the receiver 504 of FIG. 5. The output voltage, Vg, read at the output node 614 during a sampling operation can be correlated with movement of the receiver (and thus the reflected pressure wave) and be used to generate data representing an object at the platen, such as an image of the fingerprint of a finger.

In some implementations, rather than connecting the diode 608 to the output of an amplifier and rather than using a drive scheme in which RBias determines modes of operation of the ultrasonic sensor, the drive scheme can be governed by the waveform and toggling of DBias, in the example of FIG. 6. This is because the anode of the diode 608 is coupled to receive the DBias signal, and the cathode of the diode 608 is coupled with the second electrode of the capacitor 604, where the second electrode serves as a sampling terminal or sampling electrode. Thus, the diode 608 can control the mode of operation of the read circuitry 616.

Figure 7:
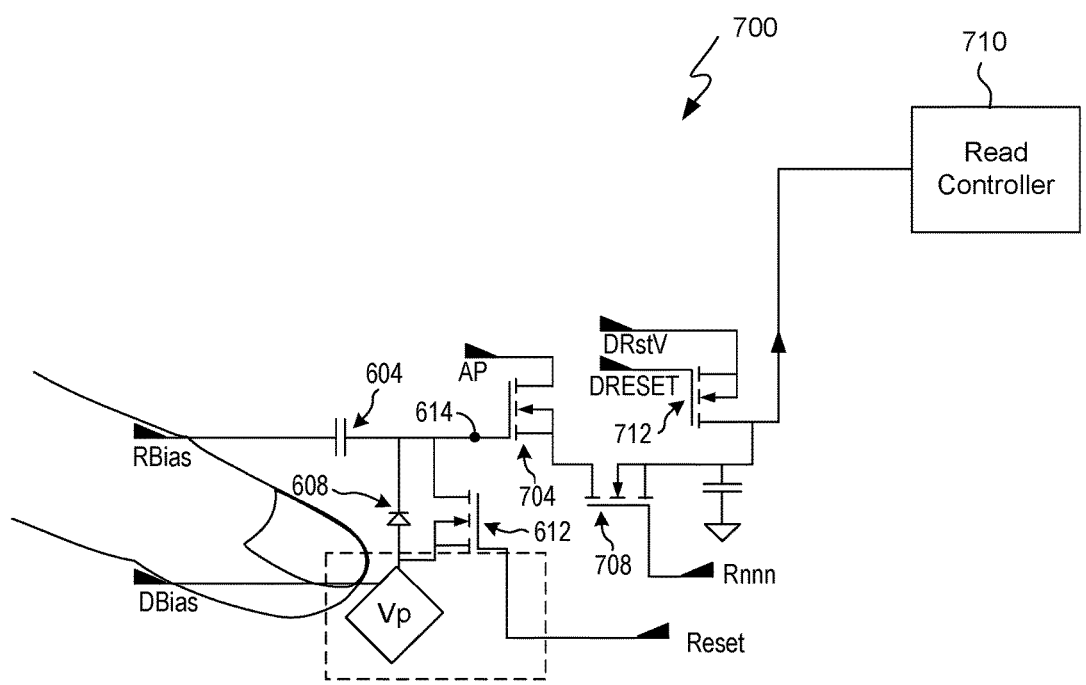
FIG. 7 shows a circuit diagram of an example of circuitry 700 combining the circuit of FIG. 6 with a read controller for reading data based on a drive scheme according to some implementations.

FIG. 7 shows a circuit diagram of an example of circuitry 700 combining the circuit of FIG. 6 with a read controller for reading data based on a drive scheme according to some implementations. In FIG. 7, the circuitry 700 includes the capacitor 604, the diode 608, and the reset transistor 612 all coupled as described above with reference to FIG. 6. In the example of FIG. 7, the transistor 612 is in the form of an NMOS TFT. In FIG. 7, the remaining transistors 704, 708 and 712 are coupled as shown in FIG. 7 and are components of the read circuitry 616 of FIG. 6. These read transistors 704, 708 and 712 are also NMOS TFTs in this example. The read transistors 704, 708 and 712 may be connected to and biased by a read controller 710 including driver circuitry providing row drivers, column drivers, etc., analog-to-digital converters, and other circuitry implemented to determine image data corresponding to an electrical signal monitored at the output node 614 during a sampling operation.

In the example of FIG. 7, the reset transistor 612 can be turned on to reset the output node 614 when a transmitter is biased to generate the pressure wave. Next, DBias can be raised to an appropriate voltage to provide the sampling operation. This allows the gate of the transistor 704 to be responsive, e.g., turned on, based on the voltage at the output node 614 that is driven by DBias and based on the rectifying provided by the diode 608. In FIG. 7, the read controller 710 can apply a read control signal to the transistor 708 to cause the transistor 708 to turn on and allow for an output signal on the gate of the transistor 704 to be transferred through the transistor 708 for reading (e.g., to determine image data).

Figure 8:
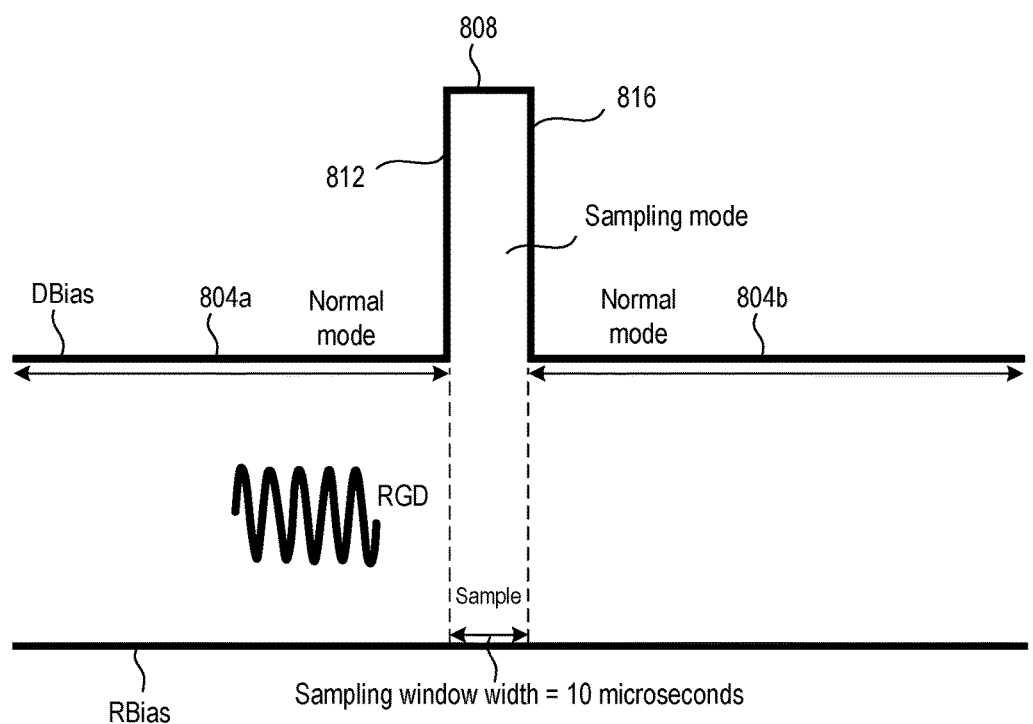
FIG. 8 shows a timing diagram including examples of signals illustrating operation of the circuitry in FIGS. 6 and 7 according to some implementations.

FIG. 8 shows a timing diagram including examples of signals illustrating operation of the circuitry in FIGS. 6 and 7 according to some implementations. In FIG. 8, RBias can be grounded, fixed at a DC voltage, floating, etc., as explained above. DBias is configured to switch between two different voltages to provide two modes of operation for the read circuitry 616 in FIG. 6: normal and sampling. In the example of FIG. 8, normal parts 804a and 804b of the DBias waveform corresponding to a lower voltage of DBias are shown, while a sampling part 808, e.g., a window, corresponding to a higher voltage of DBias is also shown. A sampling operation occurs during the sampling part 808 of DBias in FIG. 8, where DBias causes the diode 608 of FIGS. 6 and 7 to be forward biased. In this way, an electrical signal generated by the deformation of the piezoelectric material of the receiver (based on the reflected pressure wave) is provided on the bottom electrode to the output node 614, which is coupled with the cathode of the diode 608 and the read circuitry 616 of FIG. 6 as explained above. The normal operation can put the diode 608 in a reverse bias state. In the example of FIG. 8, the voltage of DBias during the normal operation is lower than the voltage during the sampling operation.

In some but not all implementations, the modes of operation are limited to two, e.g., normal and sampling in the example of FIG. 8. Such implementations can be contrasted with some conventional drive schemes in which at least a third mode of operation is provided for blocking in conjunction with an amplifier coupled with the top electrode of the ultrasonic sensor. That is, in situations where no amplifier is used to amplify an electrical signal generated at the second electrode as a result of deformation of the receiver, the third, i.e., blocking or holding operation can be omitted. A transmitter can generate the pressure wave during the normal operation, and when the desired reflected pressure wave is to be sampled, the sampling operation can be performed by properly biasing DBias.

Having a drive scheme based on toggling DBias can result in reduced area and power requirements for circuit design since amplifiers do not need to be used, and since lower voltage swings can be used for the two voltage levels of DBias, for instance, as illustrated in FIG. 8. Additionally, in some implementations, since the sampling is done on the bottom electrode, this can allow for the top electrode to be relatively uniform in thickness, and therefore, decrease the likelihood of delamination and shorts involving the platen. Additionally, the circuitry (e.g., diode and read circuitry) can be isolated from the top electrode, and therefore, be less likely to be affected by an electrostatic overstress (EOS) event due to the platen.

Moreover, in some implementations, other circuitry can be coupled with RBias since an amplifier is not coupled to the top electrode. For example, RBias can be coupled with touch circuitry (e.g., in a controller circuit or other type of circuit) and be used detect a touch on the platen. As a result, the ultrasonic sensor can be used to detect both touch of an object, such as a finger, on the platen as well as to generate an electrical signal that can be used to generate data representative of the object, such as image data.

Figure 9:
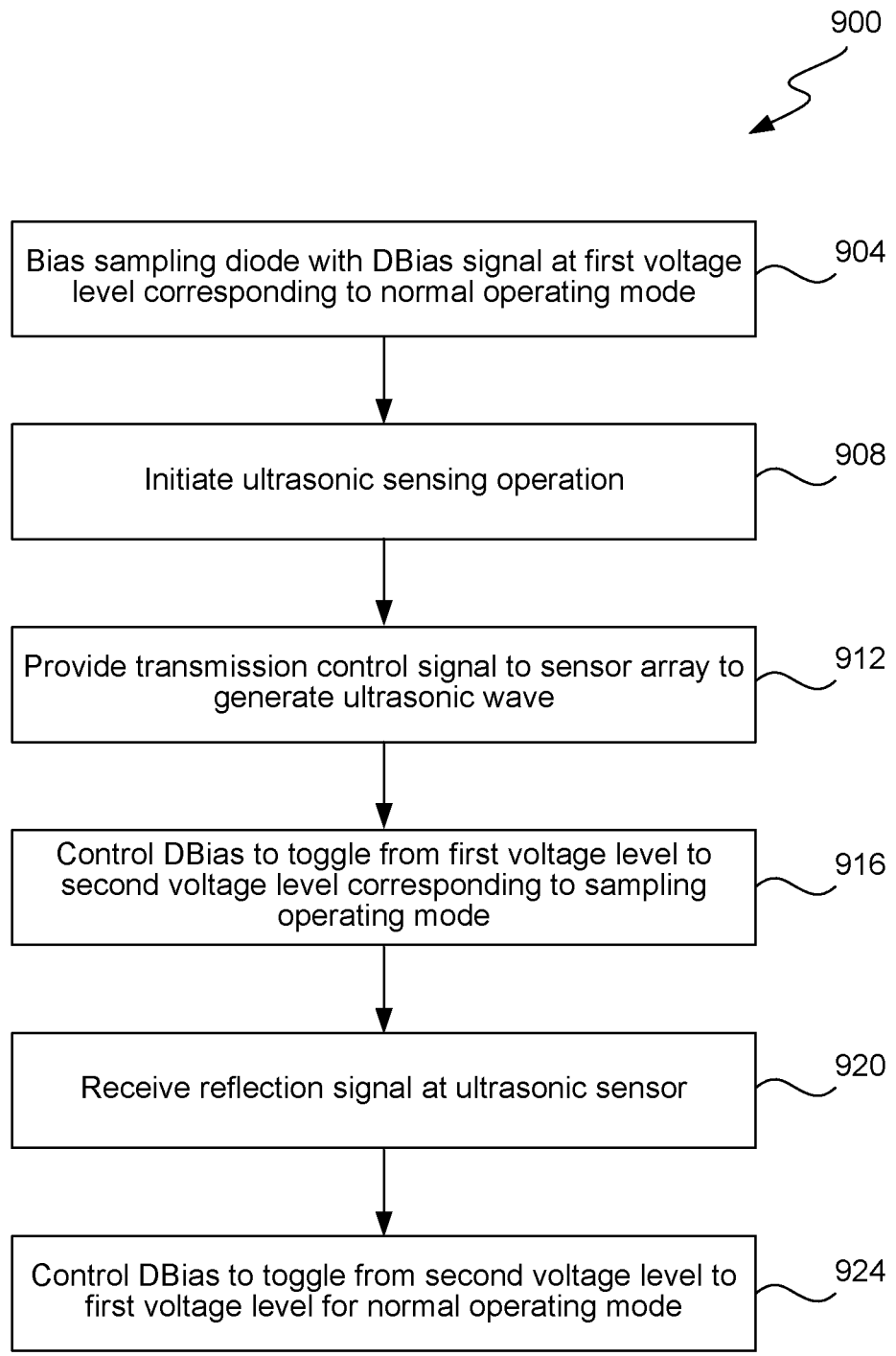
FIG. 9 shows a flow diagram of an example of a method 900 for ultrasonic sensing according to some implementations.

FIG. 9 shows a flow diagram of an example of a method 900 for ultrasonic sensing according to some implementations. One or more operations of the method 900 may be initiated by one or more of the controllers described above. At 904 of FIG. 9, a controller such as the sampling controller 532 of FIG. 5 biases the diode 524 by providing DBias to the diode 524, as explained above. DBias can have a waveform similar to that illustrated in FIG. 8, where DBias is controlled to toggle between two voltage levels to provide either a normal mode of operation or a sampling mode. In this example, DBias initially has a voltage level corresponding to normal operating mode. In FIG. 9, the method 900 further includes initiating an ultrasonic sensing operation, at 908. For example, returning to FIG. 2B, the controller 214 may receive a command from the processor 220 indicating that the controller 214 is to initiate the ultrasonic sensing operation.

At 912 of FIG. 9, a transmission control signal is provided to the ultrasonic sensor or an entire ultrasonic sensor array 212 of FIG. 2B. This transmission control signal can be generated using a resonator circuit in some implementations. For instance, the transmission control signal can be in the form of a burst signal provided to a transmitter of the ultrasonic transducer to initiate generation of a main burst of the ultrasonic wave. At 916, a controller causes operation to transition from the normal mode to the sampling mode, for instance, by toggling the voltage of DBias from one level to another as illustrated by the rising edge 812 in the example of FIG. 8. This transition causes the piezoelectric material to operate according to a sample mode of operation.

In FIG. 9, at 920, a reflection signal is received at the sensor array. The reflection signal may be generated by the ultrasonic sensor based on a reflection of the ultrasonic wave, as explained above. At 924, DBias is controlled to cause operation to toggle back to normal mode after the reflection signal is received, as illustrated by falling edge 816 in the example of FIG. 8.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module that may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

What is claimed is:

1. An apparatus comprising:
a piezoelectric ultrasonic transducer having a first electrode, a second electrode, and a piezoelectric layer disposed between the first and second electrodes, the second electrode being coupled with a sampling node, wherein the first electrode is configured to receive a receive bias signal;
a sampling diode having an input and an output, the input coupled to receive a diode bias signal, the output coupled with the sampling node;
controller circuitry configured to control the diode bias signal to at least partially drive a voltage at the sampling node; and
read circuitry coupled with the sampling node to read the voltage,
wherein the controller circuitry is configured to control the diode bias signal to switch between two voltage levels comprising a first level and a second level, the first level being a non-zero voltage level that corresponds to a normal mode of operation of the read circuitry and the second level being a non-zero voltage level that corresponds to a sampling mode of operation of the read circuitry, and wherein the first level is different from the second level and from a voltage level of the receive bias signal, and wherein the second level is different from the first level and from the voltage level of the receive bias signal.

2. The apparatus of claim 1, wherein the controller circuitry is configured to assert the second level during a sampling window corresponding to activation of the read circuitry.

3. The apparatus of claim 1, further comprising a substrate disposed adjacent to the second electrode opposite the piezoelectric layer, the substrate being a thin-film transistor (TFT) layer and comprising the sampling diode.

4. The apparatus of claim 3, further comprising a reset transistor formed in the TFT layer and coupled with the sampling diode to control resetting of the voltage.

5. The apparatus of claim 1, wherein the first electrode is coupled with one of: a ground terminal, a DC voltage source or a fixed AC voltage source.

6. The apparatus of claim 1, wherein the first electrode is floating.

7. The apparatus of claim 1, further comprising a touch controller coupled with the first electrode, the touch controller configured to provide touch control of the piezoelectric layer.

8. The apparatus of claim 1, further comprising a platen disposed adjacent to the first electrode opposite the piezoelectric layer.

9. A method comprising:
providing a diode bias signal to a sampling diode coupled with a sampling node;
providing a receive bias signal to a first electrode;
initiating transmission of an ultrasonic signal using a piezoelectric ultrasonic transducer having the first electrode, a second electrode, and a piezoelectric layer disposed between the first and second electrodes, the second electrode being coupled with the sampling node, the piezoelectric ultrasonic transducer capable of receiving a reflected portion of the ultrasonic signal and generating a response characteristic based on the reflected portion of the ultrasonic signal;
controlling the diode bias signal to bias the diode in association with a temporary transition of a mode of operation from a normal mode to a sampling mode, the diode bias signal being driven to a first level corresponding to the normal mode and a second level corresponding to the sampling mode, wherein the first level is a non-zero voltage level that is different from the second level and from a voltage level of the receive bias signal, and wherein the second level is a non-zero voltage level that is different from the first level and from the voltage level of the receive bias signal; and
enabling sampling, during the sampling mode of operation, of an electrical signal at the sampling node.

10. The method of claim 9, wherein read circuitry is controlled to perform the sampling during the sampling mode of operation.

11. The method of claim 9, further comprising:
resetting a voltage at the sampling node using a reset switch coupled with the diode.

12. The method of claim 9, wherein a substrate is disposed adjacent to the second electrode opposite the piezoelectric layer, the substrate being a thin-film transistor (TFT) layer and comprising the sampling diode.

13. A non-transitory computer readable medium storing program code to be executed by one or more processors, the program code comprising instructions configured to cause:
providing a diode bias signal to a sampling diode coupled with a sampling node;
providing a receive bias signal to a first electrode;
initiating transmission of an ultrasonic signal using a piezoelectric ultrasonic transducer having the first electrode, a second electrode, and a piezoelectric layer disposed between the first and second electrodes, the second electrode being coupled with the sampling node, the piezoelectric ultrasonic transducer capable of receiving a reflected portion of the ultrasonic signal and generating a response characteristic based on the reflected portion of the ultrasonic signal;

controlling the diode bias signal to bias the diode in association with a temporary transition of a mode of operation from a normal mode to a sampling mode, the diode bias signal being driven to a first level corresponding to the normal mode and a second level corresponding to the sampling mode, wherein the first level is a non-zero voltage level that is different from the second level and from a voltage level of the receive bias signal, and wherein the second level is a non-zero voltage level that is different from the first level and from the voltage level of the receive bias signal; and enabling sampling, during the sampling mode of operation, of an electrical signal at the sampling node.

14. The computer readable medium of claim 13, the instructions further configured to cause:

resetting a voltage at the sampling node using a reset switch coupled to the diode.

15. An apparatus comprising:

transducer means for generating an ultrasonic wave and receiving a reflected portion of the wave, the transducer means having a first electrode, a second electrode, and a piezoelectric layer disposed between the first and second electrodes, the first electrode configured to receive a receive bias signal, the second electrode being coupled with a sampling node;

diode bias means for at least partially driving an electrical signal at the sampling node, the diode bias means coupled with the sampling node, the diode bias means providing a diode bias signal to a sampling diode at a first level corresponding to a normal mode of operation and a second level corresponding to a sampling mode of operation, wherein the first level is a non-zero voltage level that is different from the second level and from a voltage level of the receive bias signal, and wherein the second level is a non-zero voltage level that is different from the first level and from the voltage level of the receive bias signal; and reading means for reading the electrical signal, the reading means coupled with the sampling node.

* * * * *